(12) United States Patent
Wischerhoff

(10) Patent No.: US 7,229,840 B1
(45) Date of Patent: Jun. 12, 2007

(54) SURFACES COMPRISING A HYDROPHILIC SPACER, COVALENTLY BONDED TO HYDROGELS

(75) Inventor: Erik Wischerhoff, Bunnik (NL)

(73) Assignee: Andreas Hofmann, Wallenfels (DE)

( * ) Notice: Subject to any disclaimer, the term of this patent is extended or adjusted under 35 U.S.C. 154(b) by 454 days.

(21) Appl. No.: 10/415,306

(22) PCT Filed: Nov. 2, 2000

(86) PCT No.: PCT/EP00/10810

§ 371 (c)(1),
(2), (4) Date: Jul. 28, 2003

(87) PCT Pub. No.: WO02/37107

PCT Pub. Date: May 10, 2002

(51) Int. Cl.
*G01N 33/543* (2006.01)
(52) U.S. Cl. .................. 436/518; 385/12; 385/129; 385/130; 385/131; 422/82.05; 422/82.11; 435/287.1; 435/287.2; 435/288.7; 435/808; 436/525; 436/528; 436/529; 436/531; 436/805
(58) Field of Classification Search .............. 385/12, 385/129, 130, 131; 422/82.05, 82.11; 435/287.1, 435/287.2, 288.7, 808; 436/518, 525, 528, 436/529, 531, 805
See application file for complete search history.

(56) References Cited

U.S. PATENT DOCUMENTS 5,242,828 A * 9/1993 Bergstrom et al. ........ 435/287.1
5,395,587 A    3/1995 Brigham-Burke
5,519,142 A    5/1996 Hoess

FOREIGN PATENT DOCUMENTS

| DE | 198 17 180 A | 10/1999 |
| DE | 199 16 638 A | 11/2000 |
| WO | 92 03732 A | 3/1992 |

OTHER PUBLICATIONS

O'Shannessy D et al: "Immobilization Chemistries Suitable . . . " Analytical Biochemistry, Academic Press, San Diego, CA, US, vol. 205, No. 1, Aug. 15, 1992, pp. 132-136.

(Continued)

*Primary Examiner*—Christopher L. Chin
(74) *Attorney, Agent, or Firm*—Michael J. Striker

(57) ABSTRACT

The object with the funtionalized hydrogel surface for detection of analyte molecules is obtainable by a process including (1) providing a hydrogel layer on a base surface; (2) bonding organic molecules to the hydrogel layer, each including a chain of atoms with a chain length of at least 8 atoms and a terminal group, which is an amine group, a carboxylic acid group, or a derivative thereof, and (3) reacting the terminal group with a receptor molecule that contains at least three groups, each of which is an amine group, a carboxylic acid group, a sulfonic acid group, a phosphoric acid group, a phosphonic acid group, or a derivative thereof. The receptor molecule can be a protein and the hydrogel can include a water-swellable organic polymer. A method of detecting analyte molecules, for example by surface resonance spectroscopy, is also part of the invention.

20 Claims, 2 Drawing Sheets

OTHER PUBLICATIONS

Johnson B et al: "Immobilization of Proteins to A . . . " Analytical Biochemistry, Academic Press, San Diego, CA, US, vol. 198, No. 21,Nov. 1, 1991, pp. 268-277.

F. Kretschmann et al: "Radiative Decay of Non Radiative Surface. . ." Institut Fuer Angewanite Physik der Universitaet Hamburg, Z. Naturforscil, 23, 1968, pp. 2135-2136 (in English).

Daniela D. Schlereth: "Surface-Modified Gold. . . " Journal of Electroanalytical Chemistry 425, 1997, pp. 77-85 (in English).

Lar Bertlisson et al: "Cibacron Blue. . ." Diosensors & Bioelectronics, vol. 12, No. 8. 1997, pp. 839-852 (in English).

Th Wink et al: "Self-Assembled Monolayers. ." Analyst, Apr. 1997, vol. 122, pp. 43R-50R (in English).

Jan H. Elam et al: "Covalent Coupling of. . ." Journal of Biomedical Materials Research, vol. 19, 1984, pp. 953-959 (in English).

Stefan Loefa et al: "A Novel Hydrogel Matrix. . ." J. Chem. Soc., Chem. Commun, 1990, pp. 1526-1528 (in English).

Kevin L. Prime et al: "Adsorption of Proteins. ." J. Am. Chem. Soc., 1993, 115, pp. 10714-10721 (in English).

A. J. Pertsin et al: "Law-Energy Cnfigurations of. . . " J. Phys. Chem. B. 1998, 102, pp. 4918-4926 (in English).

* cited by examiner

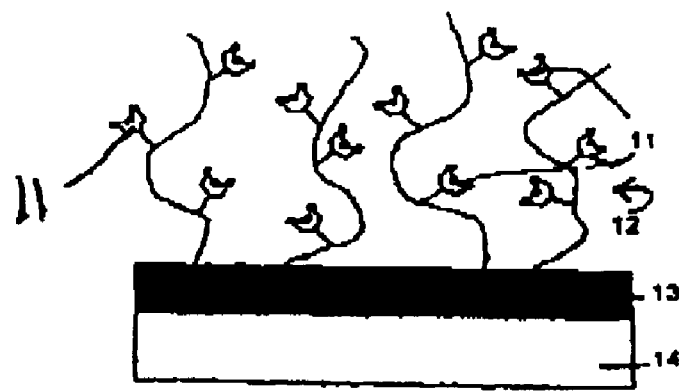
FIGURE 1   PRIOR ART
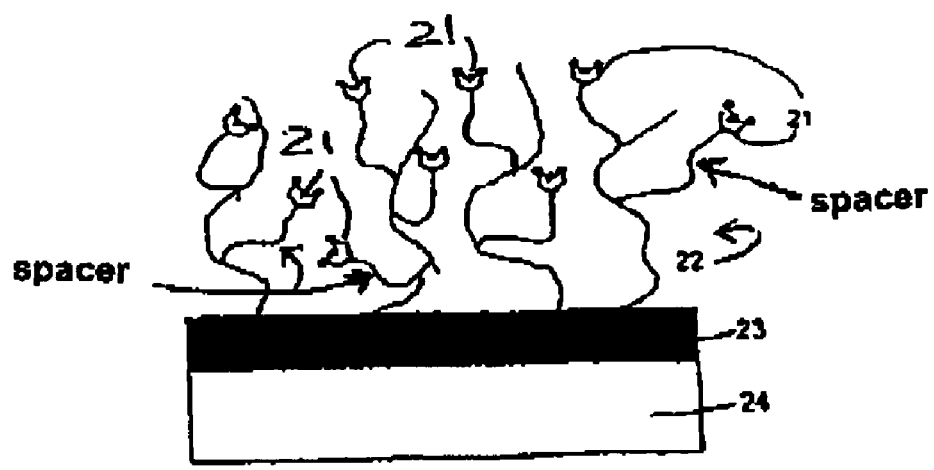
FIGURE 2

SURFACES COMPRISING A HYDROPHILIC SPACER, COVALENTLY BONDED TO HYDROGELS

CROSS-REFERENCE

This is the US National Stage of PCT/EP 00/10810, filed Nov. 2, 2000, in Europe.

BACKGROUND OF THE INVENTION

During the last ten years, there has been a great development in the technology of optical biosensors based on surface plasmon resonance (SPR) spectroscopy, so that a range of such devices have now gained an established market position (Biacore, Texas Instruments, Intersens, BioTuL). The sensor surfaces of these and other biosensors, which are responsible for the transduction of a biospecific recognition reaction of an analyte, are often provided with a functionalized polysaccharide layer or a layer of another hydrophilic polymer, which on the one hand make it possible to bind receptor molecules covalently via functional groups (B. Johnsson, S. Löfås & G. Lindquist, Anal. Biochem. 198 (1991), 268) and, on the other hand, fulfill the function of preventing non-specific adsorption of sample components (EP-B-589 867 or German Patent Application 198 17 180.3). The nature of the hydrophilic polymer layer on the surface is that of a hydrogel, so that it is swellable as well as flexible. Both properties are desirable for the function of this layer, since on and in it receptor molecules are fixed which need to be bound so flexibly that, after immobilization, they are still capable of binding analyte molecules.

Besides the use of hydrogels, it is also customary to covalently bind receptor molecules via flexible molecules—so-called spacers—directly to sensor surfaces. From binding experiments on monolayer systems, which, owing to the principle of their construction, are substantially less flexible than hydrogels, it is known that the spacer length is crucial both for the reactivity of functional groups and for the specific binding behavior (D. D. Schlereth, J. Electroanal. Chem. 425 (1997), 77; L. Bertilsson, H. J. Butt, G. Nelles, D. D. Schlereth, Biosensors & Bioelectronics 12 (1997), 839; T. Wink, S. J. van Zuilen, A. Bult, W. P. van Bennekom, Analyst 122, 43R (1997)).

Other than in such non-swellable and only moderately flexible monolayer systems, the spacer length between the hydrogel and receptors has not hitherto received attention. No influence of the chain length on the binding behavior of the ligand molecules to the receptor was suspected, since the hydrogel per se is in any event flexible. The hitherto known hydrogels on biosensor surfaces therefore have the schematic structure shown in FIG. 1. The surface of the sensor comprises a metal layer 14, to which optionally one or more interlayers 13 are applied. The receptor 11 is bound to the hydrogel 12 via a short, inflexible spacer.

The binding of receptor molecules to the hydrogel layer may be either directed or undirected. In the case of directed binding, the receptor molecule usually has only one residue, or possibly only a few (for example fewer than three) residues of the same type, which can be reacted with the optionally derivatized hydrogel. The resulting directed binding is therefore accurately defined spatially. The receptor molecules often need to be derivatized before the reaction, so that they have a suitable reactive residue. In the case of undirected binding, however, the receptor molecule has a plurality of (for example at least three) residues of the same type, which can be reacted with the optionally derivatized hydrogel. Since only one of these residues reacts with the hydrogel, the position of the binding is spatially unpredictable. As a consequence, the binding site, or the binding sites, of the receptor is in an undefined steric arrangement with respect to the hydrogel, which in turn compromises the accessibility of these binding sites for analyte molecules and can therefore influence the binding kinetics of the analyte/receptor interactions.

U.S. Pat. No. 5,395,587 uses short- and long-chained spacers for binding biotin as a receptor molecule. However, no influence of the length of the spacer is described. Furthermore, only directed binding of receptor molecules is studied, and not undirected binding.

SUMMARY OF THE INVENTION

It was an aim of the invention to provide an object, preferably a biosensor, to which a plurality of receptor molecules can be bound. No pretreatment of the receptor molecules should advantageously be necessary.

It has surprisingly been found that, in objects with a hydrogel layer, the length of the spacer between the hydrogel and receptor plays role for the binding behavior of analyte molecules in the event of undirected binding. This affords the opportunity to provide objects which allow an improved binding behavior for particular tasks. Owing to the improved accessibility due to increased flexibility, the binding behavior of the analyte molecules is more uniform despite undirected binding of the receptors, and is more similar to the behavior of the two free species in solution.

The invention therefore relates to an object with a surface, comprising a hydrogel, which can be obtained by:

(i) binding organic molecules to the hydrogel, the bound organic molecules respectively having a chain length of at least 8 atoms and a terminal residue A, selected from amine residue, carboxyl group or derivatives thereof; and (ii) reacting the terminal residue with a receptor molecule with at least three residues B of the same type, selected from amine residue, carboxyl group, sulfonic acid residue, phosphoric acid residue, phosphonic acid residue and derivatives thereof.

FIG. 2 shows a schematic representation of an object according to the invention. The object comprises a base layer 24, preferably a metal layer, on which one or more interlayers 23 are applied. A hydrogel 22 is bonded to the interlayer or interlayers 23 as described in more detail in the examples provided hereinbelow. It differs from the conventional object shown in FIG. 1 because the receptors 21 are bound to the hydrogel 22 via a long-chain spacer with a chain length of at least 8 atoms.

The invention furthermore relates to a process for producing an object with a functionalized hydrogel surface, comprising the steps:

(i) binding organic molecules to the hydrogel, the bound organic molecules respectively having a chain length of at least 8 atoms and a terminal residue A, selected from amine residue, carboxyl group or derivatives thereof; and (ii) reacting the terminal residue A with a receptor molecule with at least three residues B of the same type, selected from amine residue, carboxyl group, sulfonic acid residue, phosphoric acid residue, phosphonic acid residue and derivatives thereof.

The invention furthermore describes the use of an object according to the invention for the detection of analyte molecules.

The use is furthermore described of an object with a functionalized hydrogel surface, comprising organic molecules bound to the hydrogel, the bound organic molecules respectively having a chain length of at least 8 atoms and a terminal residue A, selected from amine residue, carboxyl group or/and [sic] derivatives thereof, for undirected binding of a receptor molecule with at least three residues B of the same type, selected from amine residue, carboxyl group, sulfonic acid residue, phosphoric acid residue, phosphonic acid residue and derivatives thereof.

BRIEF DESCRIPTION OF THE DRAWING

FIG. 1 shows a schematic representation of a conventional object with a hydrogel surface, in which the receptors are bound to the hydrogel by short spacers.

FIG. 2 shows a schematic representation of an object according to the invention with a hydrogel surface, in which the receptors are bound to the hydrogel by flexible, long-chained spacers.

DETAILED DESCRIPTION OF THE INVENTION

Figure 3:
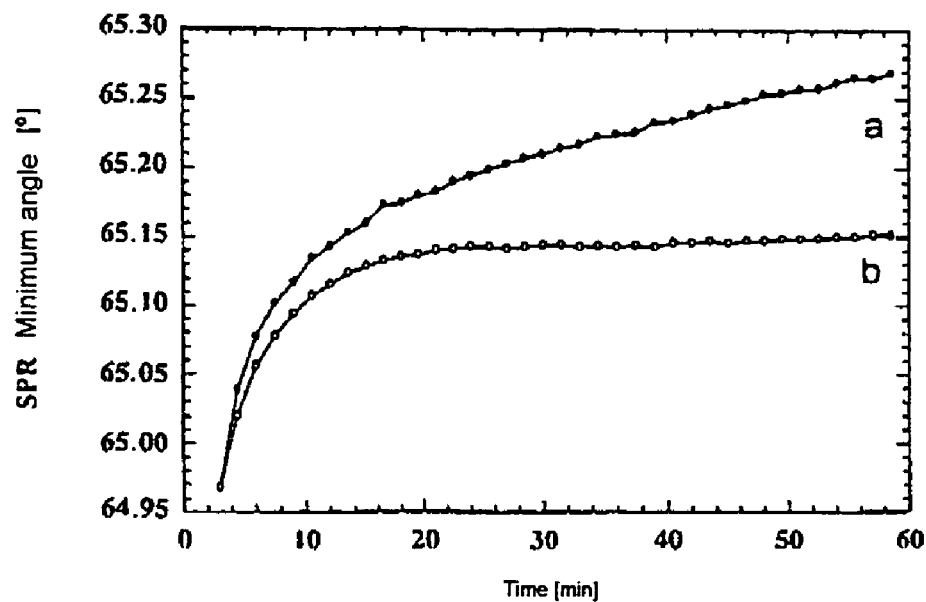
FIG. 3 shows the covalent binding of lysozyme as a function of time in the sensor (b) according to the invention and in the comparative sensor (a) of Example 1.

In order to allow a clear presentation of the relevant effect, the effect due to the modified bulk refractive index when adding the analyte is computationally removed in FIGS. 1 and 2. The effects due to modified refractive indices were measured on inert, non-functionalized surfaces (that is to say hydrogel without functional groups and receptors) and subtracted.

The objects according to the invention may be employed, for example, as sensors, above all biosensors, in a wide variety of analytical measurement methods. Examples of suitable fields of use of the objects are in affinity-based sensor technology, such as surface plasmon resonance (SPR) spectroscopy and quartz balances, as well as in interferometric measurement methods, for example reflection interference contrast microscopy and reflection interference spectroscopy. They are particularly suitable for use in SPR. The structure of the non-functionalized surface is dictated according to the analytical method in which the object according to the invention is intended to be used, and is known to the person skilled in the art (Journal of Biomedical Materials Research, 18 (953–959) (1984) and J. Chem. Soc., Chem. Commun., 1990, 1526). In the scope of the invention, the term "non-functionalized surface" is used to denote the surface of an object with the hydrogel layer before binding of the organic molecules with the residue A. The term "functionalized surface" is used to denote the surface of an object with the hydrogel layer after binding of the organic molecules with the residue A. The object according to the invention has a base surface comprising, for example, a glass, semiconductor or metal layer. Metal layers are preferred, above all noble-metal layers, for example of gold or silver, as are employed for example in SPR.

The non-functionalized object has a hydrogel layer on the surface. This layer is used to prevent non-specific adsorptions, which vitiate the measurement signal. Hydrogels are water-swellable polymers. The hydrogels may, for example, involve a polysaccharide, a derivative thereof or a swellable organic polymer such as poly{N-[tris-(hydroxymethyl)-methyl]-acrylamide}, polyvinyl alcohol or polyethylene glycol. Polysaccharides are preferred. Derivatives include amino derivatives or carboxyalkyl derivatives, the alkyl residue preferably having from 1 to 4 carbon atoms. Examples of polysaccharides are amylose, inulin, pullulan or dextran. Pullulan or dextran and derivatives thereof are particularly preferred. Dextran and derivatives thereof are particularly preferred. Carboxymethyldextran is preferably used.

The hydrogel layer should be a few nanometers thick when dry, and swells in an aqueous medium to a thickness of about 100 nm, so that the surface is fully covered. The swollen polymer layer simulates the natural environment of biomolecules, and is suitable to prevent denaturing and therefore inactivation of the biomolecules. The adsorption of molecules other than those to be analyzed is also effectively prevented. The swollen hydrogel layer is furthermore capable of compensating for irregularities of the surface. The binding of biomolecules also takes place in the swollen matrix, and not only directly on the surface. This reduces the importance of surface irregularities, which otherwise contribute to a poorly defined surface and therefore to poorly quantifiable measurement results.

Methods for coating surfaces with hydrogels are known (J. of Biomedical Materials Research, 18, 953 (1984), DE-A 198 17 180). For example, a correspondingly prepared surface (DE-A 198 17 180, EP-B-0 589 867) is put for between 1 h and 5 h, typically 3 h, into a corresponding freshly prepared aqueous hydrogel solution made of hydroxy polymer. The concentration of the hydroxy polymer in the solution is between 10 and 500 mg·ml$^{-1}$.

Organic molecules, which have a residue A, are bound to this non-functionalized hydrogel layer. The bound organic molecules have a terminal residue A selected from amine residue, carboxyl group and derivatives thereof. Although primary amine residues are preferred, it is also possible to use secondary amine residues with a $C_{1-4}$ hydrocarbon residue. Besides carboxyl groups, it is possible to use, for example, anhydrides and carboxylic acid halides, such as carboxylic acid chloride. The terminal residue A is preferably a carboxyl group.

The bound organic molecules respectively have a chain length of at least 8 atoms. The binding behavior of analyte molecules can be influenced by means of the length of the chain. The chain preferably has from 8 to 40 atoms, more preferably from 10 to 20 atoms. The chain may be a substituted or unsubstituted, branched or unbranched hydrocarbon chain. The chain is preferably linear. These chains are preferably themselves hydrophilic. Long alkyl chains or aromatic residues in the chain, or as substituents on it, are less suitable since they could also cause non-specific adsorption via hydrophobic interactions. The hydrophilic nature of the spacers can be adjusted by incorporating oligo-ethylene oxide units (K. L. Prime & G. M. Whitesides, J. Am. Chem. Soc. 115 (1993), 10714, A. J. Pertsin, M. Grunze & I. A. Garbuzova, J. Phys. Chem. B 102 (1998), 4843) or by integrating hydrophilic residues such as amide groups. For instance, in order to increase the hydrophilicity of the chain, up to 70% of the carbon atoms may be replaced by N, S or non-peroxidic O, preferably N or non-peroxidic O. From 10 to 50% of the carbon atoms are preferably replaced by said heteroatoms. Possible substituents are $C_{1-4}$ hydrocarbon residues, such as alkyl or alkylene residues, and known hydrophilic substituents such as hydroxyl groups and carbonyl-bound oxygen atoms, and the substituents are preferably hydrophilic. Insofar as they cannot be used as terminal residues A, it is also possible for amine residues, carboxyl groups and derivatives thereof to be used as substituents. The substituents used in the scope of the invention should not be selected in terms of either type or number in such a way that they compromise the flexibility of the organic molecules, which is important according to the invention.

The chain length is the number of C, N, O and S atoms, starting from the hydrogel, in the main chain as far as the terminal residue, the latter being included. If a part of the terminal residue is cleaved during the binding of the receptor molecule, then the cleaved atoms are not counted. When counting, only the atoms of the organic molecules and the atoms which, for example, are due to the derivatization of the hydrogel are counted.

The reaction conditions for coupling the organic molecules to the hydrogel layer vary as a function of the chosen compound. Examples of these reaction conditions will be described below in the preferred embodiments and the examples.

The receptor molecule is used for specific binding of the analyte molecule. It is therefore in general a biomolecule. Examples of suitable receptor molecules are proteins, nucleic acids and biologically active oligo- or polysaccharides. Proteins are preferred. The invention relates to the undirected binding of receptors to a hydrogel surface. The receptor molecules consequently have at least 3, preferably at least 5, more preferably at least 10 residues B of the same type. The maximum number of residues B is not restricted, but the receptor molecule should be soluble in the solvent being used. The receptor molecule preferably has at most 10,000, more preferably at most 1000 residues B. The reactivity of the residues of the same type need not be identical, although it is of the same order of magnitude. The residues B are selected from amine residue, carboxyl group, sulfonic acid residue, phosphoric acid residue, phosphonic acid residue and derivatives thereof. Possible derivatives must not hinder the reaction with the terminal residue A of the organic molecules, [sic] Suitable derivatives are, for example, ester derivatives of said acids with at least one —OH group, in order to permit reaction with the residue A. It is of course also possible to use activated forms, which, for example, may be obtained by reacting amine residues with ethyl-3,3'-dimethylaminopropylcarbodiimide (EDC) and N-hydroxysuccinimide (NHS).

Analyte molecules react selectively with the receptors being used. They, therefore, are also usually biomolecules. Suitable analyte molecules are proteins, nucleic acids and biologically active oligo- or polysaccharides. Proteins are preferred.

The conditions under which the covalent binding of the analyte molecule to the receptor takes place vary as a function of the chosen system. The binding typically takes place at room temperature in buffered aqueous solutions, which have an analyte concentration in the range from 0.5 to 200 µg/ml and roughly a 100 mM buffer concentration, for example of a phosphate buffer. The reaction time is typically from 10 minutes to 2 hours.

A preferred embodiment is given in the scheme below (see also the example).

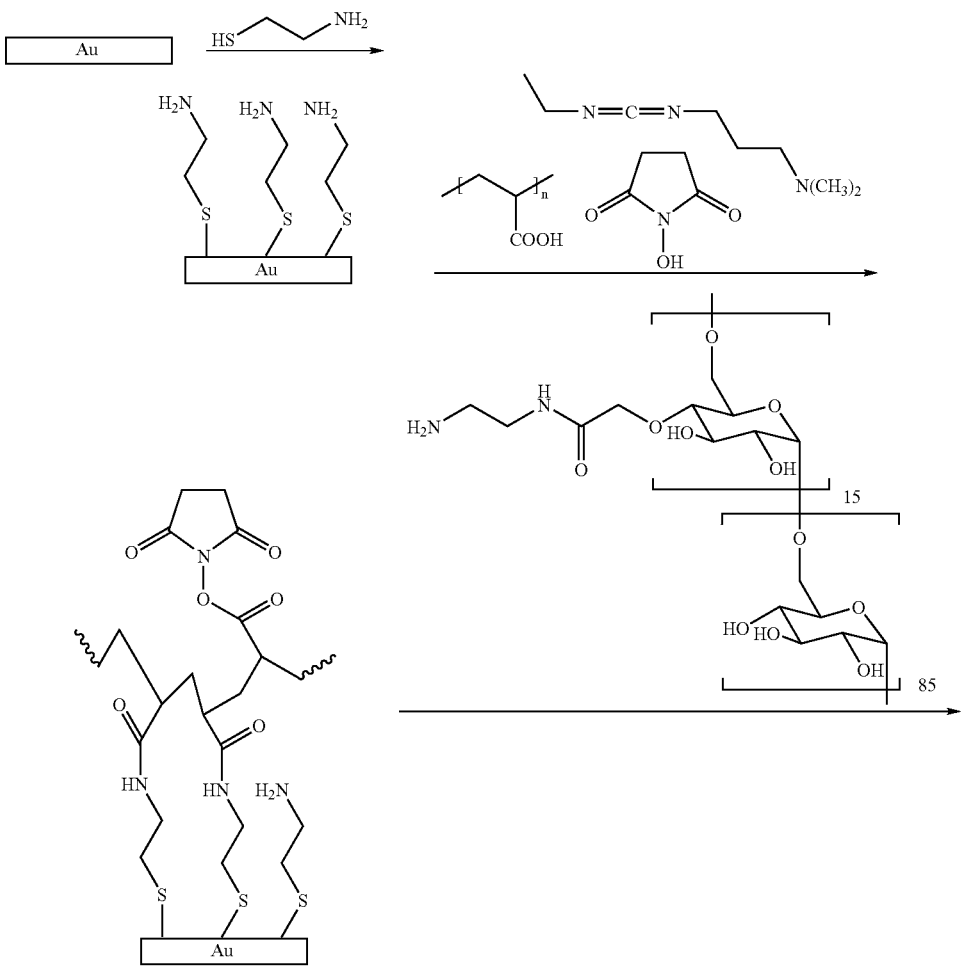

-continued
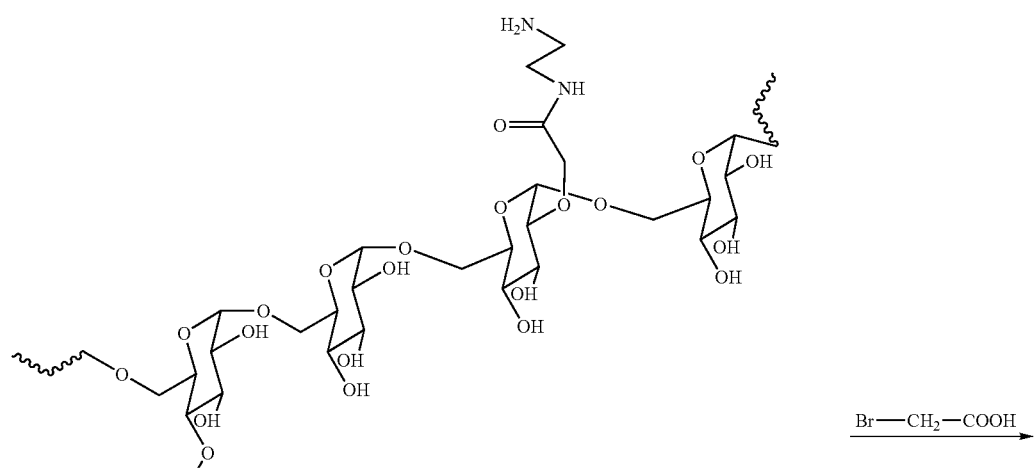
Br—CH₂—COOH →
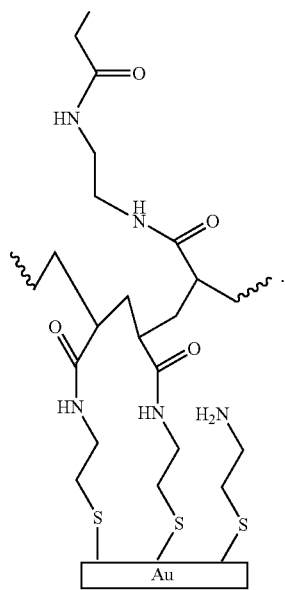
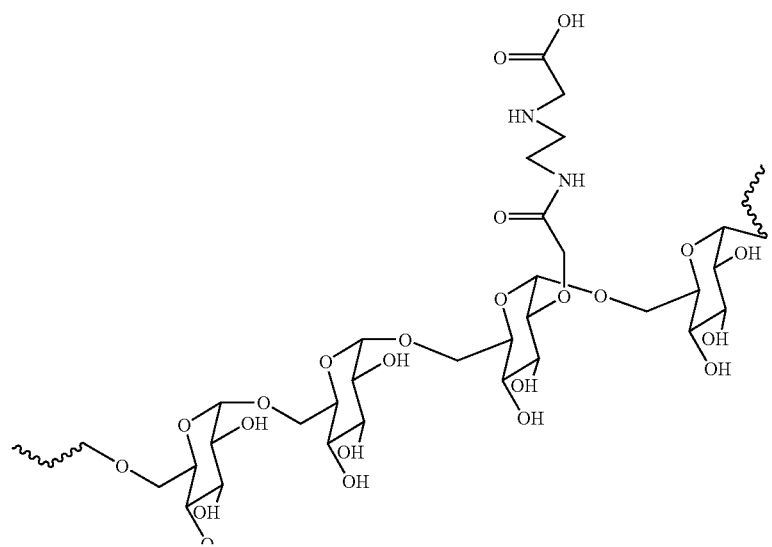

-continued

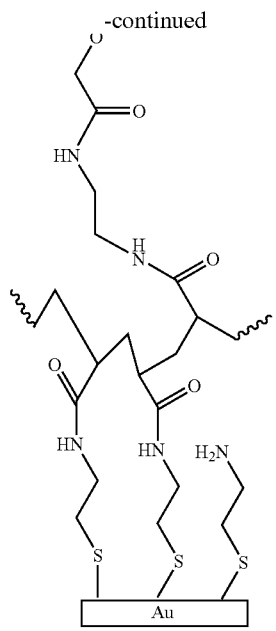

A monolayer of cysteamine is first applied to the noble-metal surface (for example gold), in which [sic] the noble-metal surface is put into an aqueous solution of from $10^{-3}$ to $5·10^{-2}$ mol·l$^{-1}$ of cysteaminium hydrochloride for 12 to 36 h. The monolayer is then reacted with polyacrylic acid, and this is activated with EDC and NHS. This reaction typically takes place with a solution consisting of $10^{-2}$ to $10^{-1}$ mol·l$^{-1}$ of polyacrylic acid with a number-average molecular weight of from 20,000 to 500,000 and corresponding amounts of EDC and NHS, which are equimolar with the COOH groups of the polymer. The solvent used is advantageously a polar solvent, such as DMSO and/or water. The reaction time is generally from 30 min to 2 h.

In a subsequent step, the polyacrylic acid is reacted with an aqueous solution of a hydrogel, typically for from 15 min to 2 h. In the scheme, carboxymethyldextran is shown as an example of the hydrogel. In this embodiment, the organic molecules are built up in two reaction steps. First, before the binding of the carboxymethyldextran to the surface, the carboxy groups are reacted with 1,2-diaminoethane. Next, after the binding of the hydrogel to the surface, the terminal carboxylic end group is introduced by reacting the amino group with bromoacetic acid. A 0.5 mol·l$^{-1}$ to 3 mol·l$^{-1}$ bromoacetic acid solution with a pH of about 14 is customarily used for the derivatization. The derivatization generally lasts from 10 to 20 h. It is of course also possible to link the organic molecules to the hydrogel in a single reaction step. This functionalization may take place either before or after the binding of the hydrogel to the surface. In this preferred embodiment, the length of the spacer is 8 atoms. The C, N and O atoms of the spacer consisting of —CH$_2$—CO—NH—CH$_2$—CH$_2$—NH—CH$_2$—CO—OH are counted, but the O of the —C(O)OH group is not counted, since it is replaced during the subsequent reaction, for example with an amine group of the analyte.

A further preferred embodiment is:

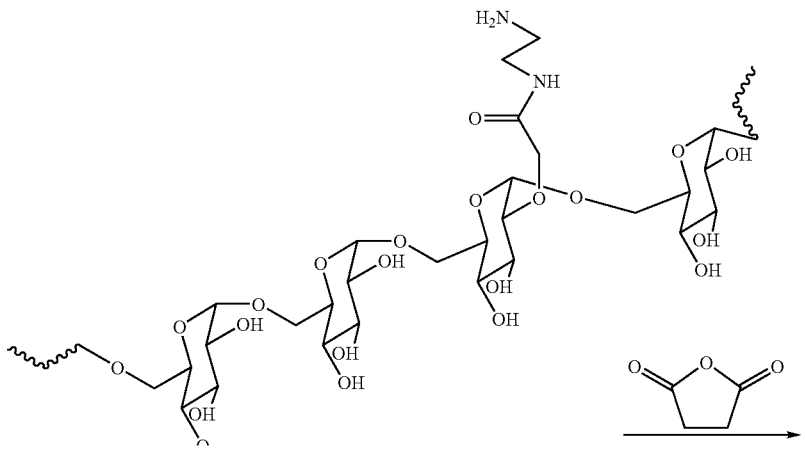

-continued
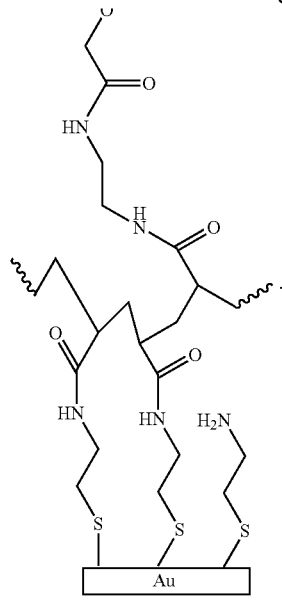
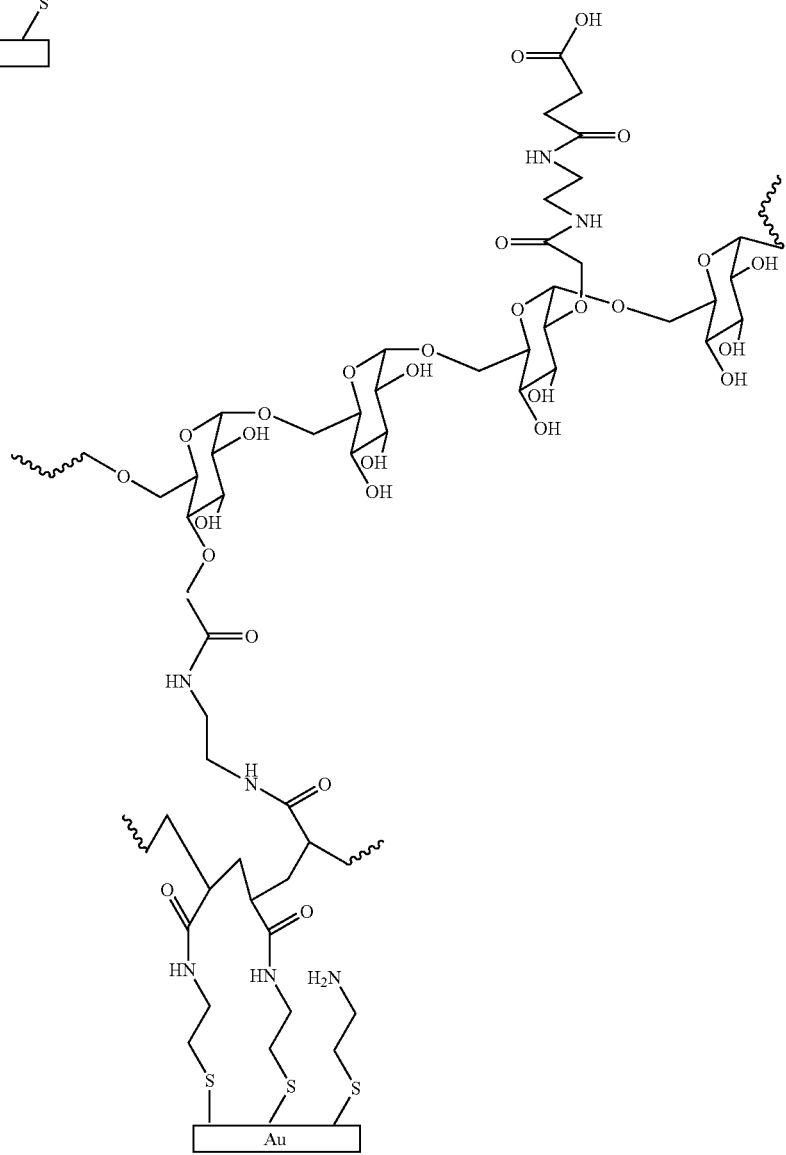

The reaction with succinic anhydride may take place in a $10^{-2}$ to $10^{-1}$ mol·l$^{-1}$ succinic anhydride solution. The reaction time is usually from 4 to 24 h. The solvents used are, for example, polar aprotic solvents such as dry DMSO.
A preferred embodiment is furthermore:
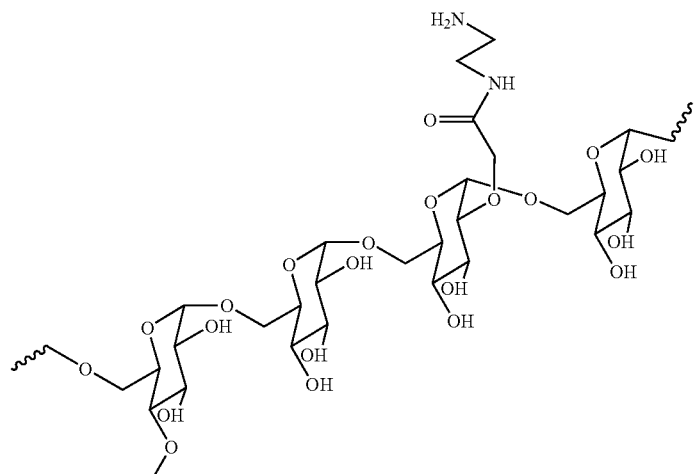
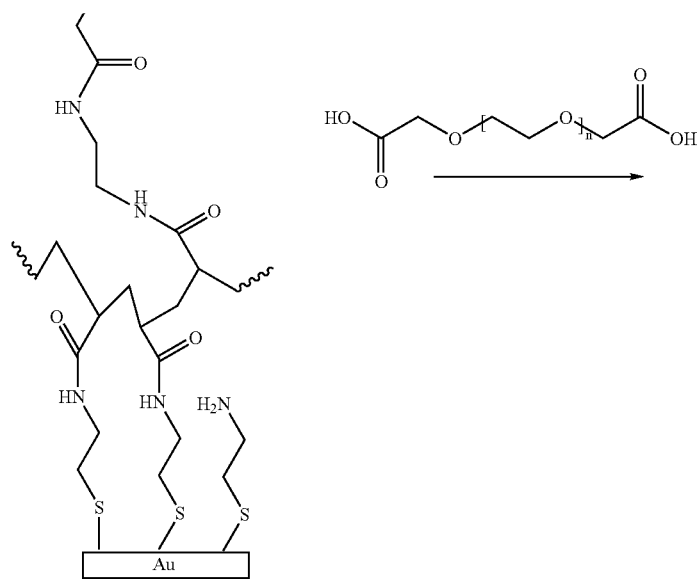
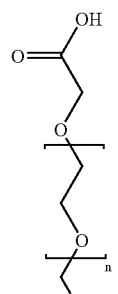

-continued
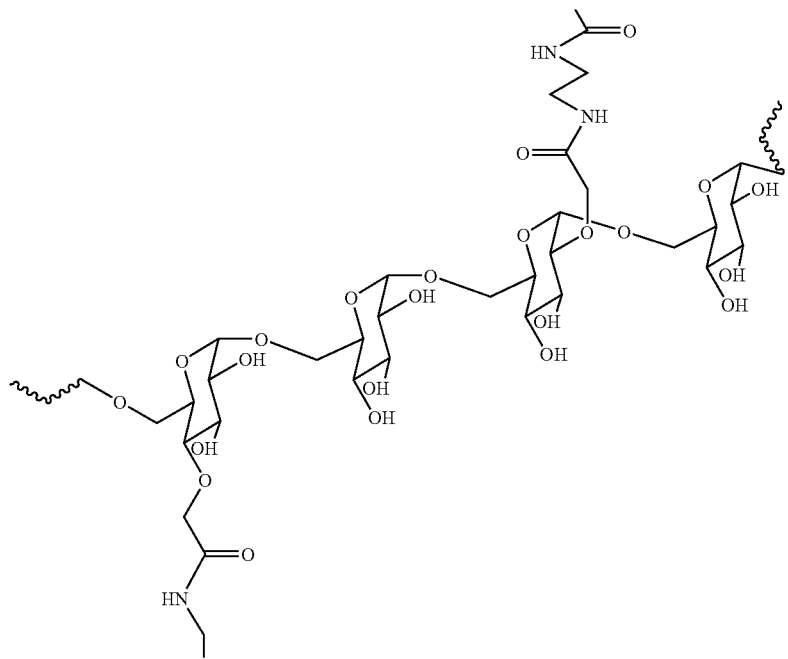
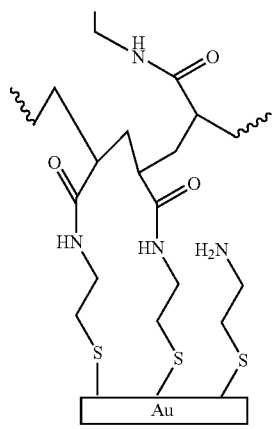

The reaction with oligo-ethylene oxide typically takes place in an aqueous solution with an oligo-ethylene oxide concentration in the range of from $10^{-2}$ to $5 \cdot 10^{-1}$ mol·l$^{-1}$ and an equimolar amount of EDC and NHS. The reaction may last from 10 min to 2 h. The oligo-ethylene oxide advantageously has n=4 to 15 repeat units.

EXAMPLE

In order to illustrate the effect of the longer spacer, two sensors are produced for surface plasmon resonance. The sensor according to the invention has the structure described in the first exemplary embodiment. A sensor with a short spacer is used as a comparative example:

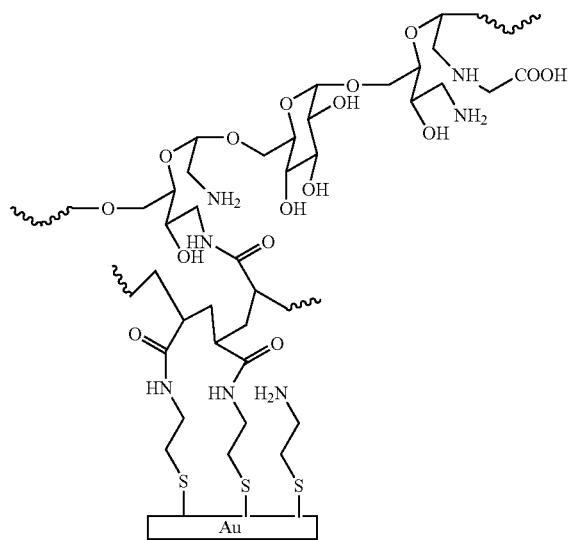

Lysozyme is used as the receptor in both sensors, and a single-chained fragment of a corresponding antibody (Hy-Hel 10 antibody) is used as the ligand.

A glass substrate with a gold surface is first put into an aqueous $2 \cdot 10^{-2}$ mol·l$^{-1}$ cysteaminium hydrochloride solution for 12 h. The substrate is then washed with ultrapure water, incubated for 5 min with 1 N NaOH and washed again with ultrapure water. An incubation solution is prepared by respectively mixing an aqueous $5 \cdot 10^{-2}$ mol·l$^{-1}$ polyacrylic acid solution (molecular weight 30,000) with solutions of 3.19 mg EDC and 4.115 mg NHS, each in 1 ml of ultrapure water. The substrate is incubated in this solution for 1 h and then washed with ultrapure water.

The hydrogel dextran is first derivatized according to the following process: 10.00 g (0.062 mol repeat unit) of dextran are dissolved with 0.99 g of NaOH (0.025 mol) and 1.71 g of bromoacetic acid (0.012 mol) in 50 ml of ultrapure water and stirred at room temperature for 24 h. The batch is then dialyzed for 3 days against distilled water, the water being changed at least five times. For further reaction, 2.40 g of ethyl-(3-dimethylaminopropyl)carbodiimide (0.0125 mol) and 1.44 g of N-hydroxysuccinimide are added to the dialyzed batch, and the mixture is stirred at room temperature for 12 h. The batch is then dialyzed again for 3 days against distilled water, the water being changed at least five times. 90% of the water is then removed at reduced pressure using a rotary evaporator, and the polymer is precipitated by introduction into ten times the volume of methanol. The yield is 9.06 g (81.5%).

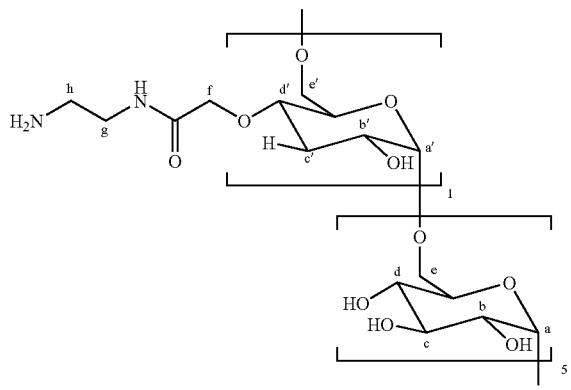

$^1$H NMR (D$_2$O, 200 MHz), δ[ppm]: 3.25 (m, H$_h$); 3.35 (m, Hg) 3.5 to 4.1 (multiple m, H$_b$, H$_c$, H$_d$, H$_e$, H$_{b'}$, H$_{c'}$, H$_{d'}$, H$_{e'}$, 5.05 (d, H$_a$, H$_{a'}$), 5.2 and 5.4 (broad signals, H$_f$)

The aminodextran which is obtained is then dissolved in water, so as to provide a 10% strength by weight solution. The substrate is put into this solution for 30 min and subsequently washed again with a large amount of ultrapure water. The substrate is then put into a solution of 1 mol·l$^{-1}$ bromoacetic acid and 2 mol·l$^{-1}$ NaOH for 12 h.

In both sensors, the hydrogel is activated for 10 min in 10 mM 4'-(2-hydroxyethyl)-1-piperazineethanesulfonic acid buffer (Hepes buffer) and 150 mM NaCl at pH 7.4 in the presence of 77 mg·ml$^{-1}$ EDC and 12 mg·ml$^{-1}$ NHS. A 0.1 mg·ml$^{-1}$ solution of lysozyme in acetate buffer at pH 4.7 is then brought into contact with the hydrogel, in order to bind the lysozyme covalently to the hydrogel by reaction between the free amino groups of the protein and activated carboxyl groups of the hydrogel.

The functionalized sensor is incorporated into an SPR device. The SPR device used is an in-house construction with θ/2θ structure (similar to E. Kretschmann and H. Raether, "Radiative Decay of Non-Radiative Surface Plasmons Exicted [sic] by Light", Z. Naturforsch., volume 23a, p. 2135 (1968)), which has an infrared laser (wavelength 784 nm) as the light source.

FIG. 3 shows the covalent binding of lysozyme as a function of time in comparative example (a) and in the sensor (b) according to the invention. The shift of the minimum to higher angles is used as an indicator for the increase in the layer thickness.

The observed shift in the SPR minimum angle ($\Delta\Theta_{pl}$) shows that the sensor according to the invention has a smaller maximum functionalization density ($\Delta\Theta_{pl}$=0.18°) than the comparative sensor ($\Delta\Theta_{pl}$=0.31°). What is essential, however, is that the rates of the two binding reactions differ from one another. In the sensor according to the invention, the binding reaction is completed after about 20 minutes, while only 71% of the possible occupation capacity is reached after this time in the comparative sensor. This behavior makes it possible to conclude that the accessibility of at least some of the terminal residues is inferior in the comparative sensor.

Figure 4:
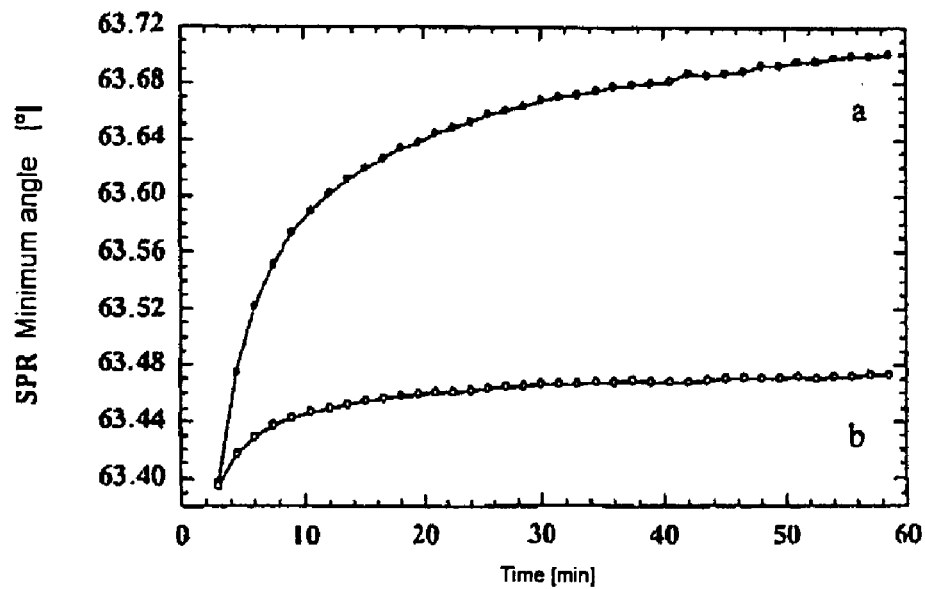
FIG. 4 shows the association reaction of a single-chained fragment antibody with lysozyme as a function of time in the sensor (b) according to the invention and in the comparative sensor (a) of Example 1.

Similar behavior is observed in the binding of the analyte. A single-chained fragment of a lysozyme antibody is used in the example. The sensor according to the invention again shows a smaller absolute occupation density ($\Delta\Theta_{pl}$=0.08°) than the comparative sensor ($\Delta\Theta_{pl}$=0.31°). In the sensor according to the invention, where the receptor molecules are bound via flexible, long-chained spacers, the association reaction is completed after about 15 minutes, while about 60 minutes elapse before saturation is reached in the comparative sensor (see FIG. 4).

Both results demonstrate a marked reactivity improvement in the sensors according to the invention. The accessibility of terminal residues and covalently bound receptors is therefore increased significantly by flexible, long-chained spacers.

The invention claimed is:

1. An object with a base surface, said object comprising a hydrogel on the base surface;
a plurality of organic spacer residues bound to said hydrogel; and
a plurality of receptors bound to said organic spacer residues;
wherein each of said organic spacer residues is attached between said hydrogel and a respective one of said receptors; each of said organic spacer residues comprises a respective chain of atoms with a corresponding chain length of at least eight atoms; each of said receptors has at least three residues (B) of the same type; and said at least three residues are each selected from the group consisting of amine groups, a carboxyl group, sulfonic acid groups, phosphoric acid groups, phosphonic acid groups, and derivatives thereof; and
wherein each of said receptors is bonded to said respective chain of said atoms by reacting a terminal group (A) of said respective chain of said atoms with a receptor molecule and wherein said terminal group (A) is selected from the group consisting of amine groups, a carboxyl group, and derivatives thereof;
so that said receptors are bound with said hydrogel in a flexible undirected manner.

2. The object as defined in claim 1, wherein the chain of the atoms is a substituted or unsubstituted, branched or unbranched hydrocarbon chain, in which optionally up to 70% of carbon atoms of said hydrocarbon chain are replaced by N, S, or non-peroxidic O atoms.

3. The object as defined in claim 1, wherein said chain length is from eight to forty atoms.

4. The object as defined in claim 1, wherein said receptor has at least five of said residues (B).

5. The object as defined in claim 1, wherein said receptor molecule is selected from the group consisting of proteins, nucleic acids, biologically active oligosaccharides, and biologically active polysaccharides.

6. The object as defined in claim 1, wherein said base surface is a glass surface, a semiconductor surface, or a metal surface.

7. The object as defined in claim 1, wherein said hydrogel comprises a water-swellable organic polymer.

8. The object as defined in claim 7, wherein said hydrogel swells to a thickness of about 100 nm over said base surface in an aqueous media.

9. The object as defined in claim 1, wherein said object is a biosensor.

10. A process for making an object with a functionalized hydrogel surface, said process comprising the steps of:
a) preparing an object with a base surface and a hydrogel layer on said base surface;
b) binding organic molecules to the hydrogel layer, wherein each of said organic molecules respectively comprise a chain of atoms with a chain length of at least 8 atoms and a terminal residue (A), wherein said terminal residue (A) is selected from the group consisting of amine groups, a carboxyl group, and derivatives thereof; and
c) reacting the terminal residue (A) of each of the organic molecules with a respective receptor molecule, said respective receptor molecule comprising at least three residues (B) of the same type, wherein each of said residues (B) is selected from the group consisting of amine groups, a carboxyl group, sulfonic acid groups, phosphoric acid groups, phosphonic acid groups, and derivatives thereof, so that said receptor molecule is bound in a flexible undirected manner with said hydrogel.

11. The process as defined in claim 10, wherein the chain of the atoms is a substituted or unsubstituted, branched or unbranched hydrocarbon chain, in which optionally up to 70% of carbon atoms of said hydrocarbon chain are replaced by N, S, or non-peroxidic O atoms.

12. The process as defined in claim 10, wherein said chain length is from eight to forty atoms.

13. The process as defined in claim 10, wherein said receptor molecule is selected from the group consisting of proteins, nucleic acids, biologically active oligosaccharides, and biologically active polysaccharides.

14. The process as defined in claim 10, wherein said base surface is a glass surface, a semiconductor surface, or a metal surface.

15. The process as defined in claim 10, wherein said hydrogel comprises a water-swellable organic polymer.

16. A biosensor obtainable by the process as defined in claim 10.

17. A method of detecting analyte molecules in an aqueous medium, said method comprising the steps of:
a) providing a biosensor comprising an object with a base layer; a hydrogel layer on the base layer; and organic residues bound to said hydrogel, said organic residues comprising respective chains with corresponding chain lengths of at least eight atoms and corresponding receptor groups bound at respective terminal positions of said chains, said receptor groups each having at least three residues (B) of the same type, and each of said three residues being selected from the group consisting of amine groups, a carboxyl group, sulfonic acid groups, phosphoric acid groups, phosphonic acid groups, and derivatives thereof; wherein said receptor groups are formed on said chains by reacting respective terminal groups (A) of said chains with corresponding receptor molecules and each of said terminal group (A) is selected from the group consisting of amine groups, a carboxyl group, and derivatives thereof; so that said receptor groups are bound in a flexible undirected manner with said hydrogel;
b) exposing the aqueous medium to the receptor groups of the biosensor provided in step a); and
c) detecting the presence of the analyte molecules, which bind with the receptor groups of the biosensor, in the aqueous medium.

18. The method as defined in claim 17, wherein said analyte molecules are detected during the detecting by surface resonance spectroscopy, quartz balance, reflection interference spectroscopy or reflection interference contrast microscopy.

19. The method as defined in claim 17, wherein said chain length is from eight to forty atoms.

20. The method as defined in claim 17, wherein said receptor molecules are each selected from the group consisting of proteins, nucleic acids, biologically active oligosaccharides, and biologically active polysaccharides.

* * * * *